(12) United States Patent
Mukhopadhyay et al.

(10) Patent No.: US 8,324,436 B2
(45) Date of Patent: *Dec. 4, 2012

(54) GAS PHASE SYNTHESIS OF 2,3,3,3-TETRAFLUORO-1-PROPENE FROM 2-CHLORO-3,3,3-TRIFLUORO-1-PROPENE

(75) Inventors: Sudip Mukhopadhyay, Berkeley, CA (US); Barbara A. Light, Niagara Falls, NY (US); Kim M. Fleming, Hamburg, NY (US); Steven D. Phillips, Buffalo, NY (US); Rajesh K. Dubey, Williamsville, NY (US)

(73) Assignee: Honeywell International Inc., Morristown, NJ (US)

( * ) Notice: Subject to any disclaimer, the term of this patent is extended or adjusted under 35 U.S.C. 154(b) by 1007 days.

This patent is subject to a terminal disclaimer.

(21) Appl. No.: 12/265,335

(22) Filed: Nov. 5, 2008

(65) Prior Publication Data

US 2009/0124837 A1   May 14, 2009
US 2012/0203036 A9   Aug. 9, 2012

Related U.S. Application Data

(63) Continuation-in-part of application No. 11/619,592, filed on Jan. 3, 2007, now Pat. No. 8,084,653.

(60) Provisional application No. 60/986,599, filed on Nov. 9, 2007, provisional application No. 60/755,485, filed on Jan. 3, 2006.

(51) Int. Cl.
*C07C 17/08* (2006.01)
(52) U.S. Cl. .................................................. 570/167
(58) Field of Classification Search ............. None
See application file for complete search history.

(56) References Cited

U.S. PATENT DOCUMENTS

| 2,931,840 | A | | 4/1960 | Marquis |
| 8,084,653 | B2 | * | 12/2011 | Mukhopadhyay ............ 570/123 |
| 2010/0036179 | A1 | * | 2/2010 | Merkel et al. ................. 570/156 |
| 2010/0137658 | A1 | * | 6/2010 | Merkel et al. ................. 570/175 |

FOREIGN PATENT DOCUMENTS

| EP | 0328148 A1 | | 8/1989 |
| JP | 6072925 A | | 3/1994 |
| WO | 2007079431 A | | 7/2007 |
| WO | WO2007079431 | * | 7/2007 |

* cited by examiner

*Primary Examiner* — Johann Richter
*Assistant Examiner* — Clinton Brooks
(74) *Attorney, Agent, or Firm* — Bruce O. Bradford

(57) ABSTRACT

A multi-step process for preparing 2,3,3,3-tetrafluoro-1-propene comprising the steps of (a) contacting a starting material comprising 2-chloro-3,3,3-trifluoro-1-propene with hydrogen fluoride in the presence of activated first catalyst selected from the group consisting of antimony-halides, iron-halides, titanium halides, and tin-halides, to produce an intermediate composition; and (b) contacting said intermediate composition with a second catalyst of activated carbon to produce a final product comprising 2,3,3,3-tetrafluoro-1-propene.

24 Claims, 1 Drawing Sheet

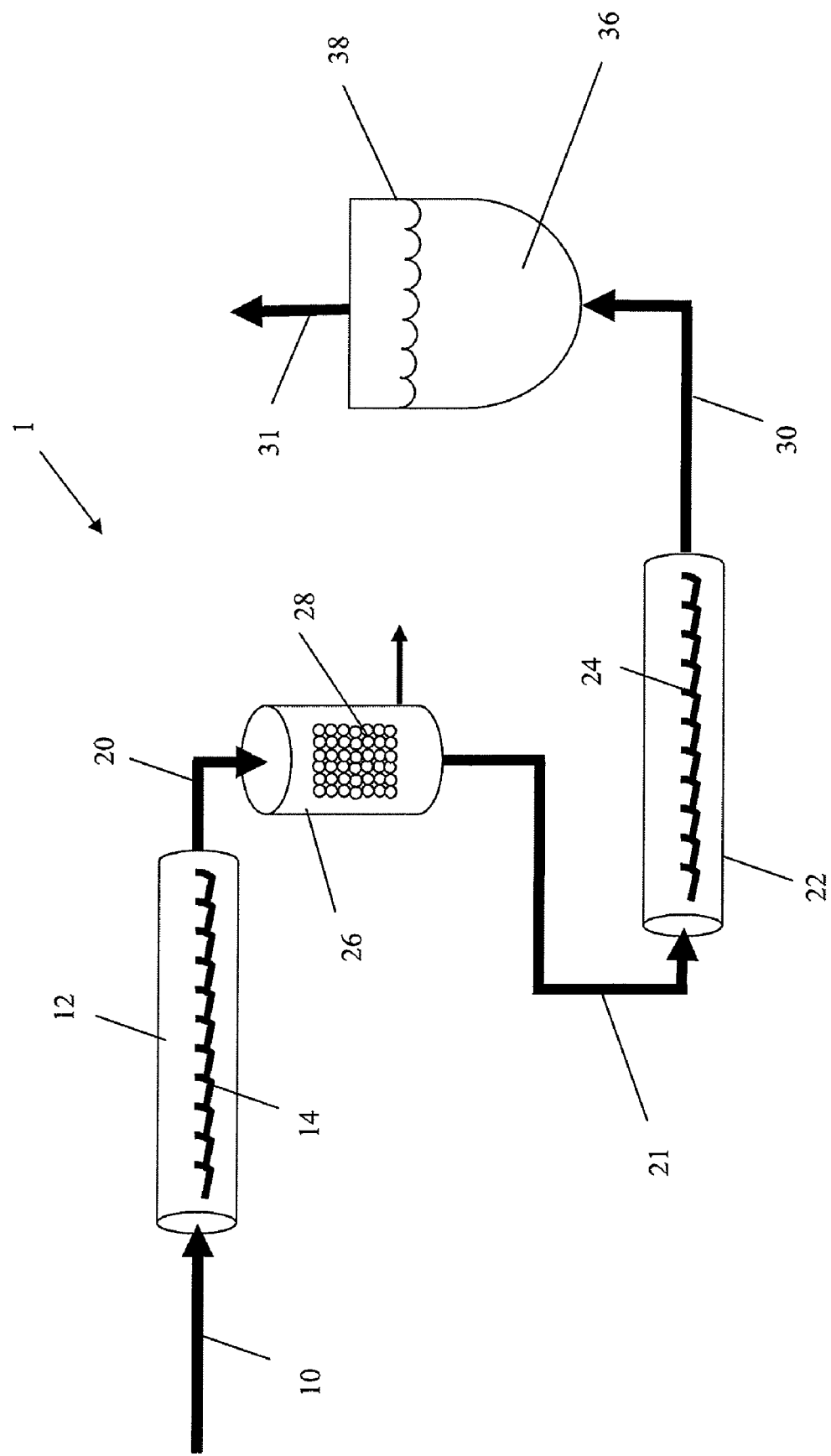

GAS PHASE SYNTHESIS OF 2,3,3,3-TETRAFLUORO-1-PROPENE FROM 2-CHLORO-3,3,3-TRIFLUORO-1-PROPENE

This application claims the priority benefit of U.S. Provisional Application No. 60/986,599, filed Nov. 9, 2007, and incorporates the same herein by reference. This application is also a continuation-in-part of U.S. application Ser. No. 11/619,592, filed Jan. 3, 2007 (now U.S. Pat. No. 8,084,653), which claims priority to U.S. Provisional Application No. 60/755,485, filed on Jan. 3, 2006.

BACKGROUND

1. Field of Invention

This invention relates to methods of synthesizing hydrofluoroolefins. More particularly, the invention relates to catalytic synthesis of 2,3,3,3-tetrafluoro-1-propene.

2. Description of Related Art

The hydrofluoroolefin 2,3,3,3-tetrafluoro-1-propene (HFO-1234yf), which can be used as a low global warming potential (GWP) refrigerant, blowing agent, etc., has been synthesized by the catalytic pyrolysis of methyl chloride and either tetrafluoroethylene or chlorodifluoromethane. For example, U.S. Pat. No. 2,931,840 describes concurrently passing 55 cc/min of MeCl and 110 cc/min $CHClF_2$ through a platinum tube (6 mm×24 in) that is heated to about 800° C. The gaseous product synthesized by this process is scrubbed to remove HCl and dried, but yields only a small amount (14.8 mole %) of 2,3,3,3-tetrafluoropropene. This low yield correlates to almost 90% of the starting material being lost to unimportant byproducts including a significant amount of carbon black, which tends to deactivate the reaction's catalyst.

EP 328148 discloses that fluorine-containing olefins having the formula $CH_2=CFR_f[R_f=(per)$ halo alkyl group)] can be prepared at low cost and with low toxic waste generation by high-temperature dehydrohalogenation and dehydration of fluoroalcohols such as $HOCH_2CF_2R_f$ in the presence of $H_2$ gas.

JP 06072925 describes the synthesis of 2,3,3,3-tetrafluoro-1-propanol by reacting tetrafluoroethylene, formaldehyde, and HF in the presence of a $TiF_4$ catalyst and limonene as a polymer inhibitor. The 2,3,3,3-tetrafluoro-1-propanol, in turn, can serve as a starting material to synthesize 2,3,3,3-tetrafluoro-1-propene (HFO-1234yf). The process of JP 06072925 involves feeding a 1:3 (mol/mol) gaseous mixture of $HOCH_2(CF_2)_4H$ and $H_2$ into a tube reactor packed with activated carbon and heated to 500° C. A residence time of 4 seconds yields $CH_2=CF(CF_2)_3H$ at a monomer conversion of 64% and a selectivity of 82%. Although this is a high-yield process, commercial handling of $H_2$ at high temperature is exceptionally hazardous. In addition, the process of JP 06072925 requires a costly on-site generation of $H_2$.

Therefore, there is a need for alternative commercial processes for producing HFO-1234yf that involving more economical and less hazardous starting materials which also result in higher conversion rates and selectivity.

SUMMARY OF THE INVENTION

Applicants have found a commercially viable process for manufacturing HFC-1234yf from HFO-1233xf that results in a conversion of over 90% and a selectivity of up to about 80%. More particularly, Applicants have found a two-step continuous gas-phase process for the production of HFO-1234yf wherein (1) relatively inexpensive HFO-1233xf is reacted with HF in the presence of a first catalyst to form an intermediate composition comprising, for example, $CF_3CFClCH_3$ and/or $CF_3CF_2CH_3$, and (2) in the presence of a second catalyst, transforming the intermediate composition into a product comprising the desired HFO-1234yf.

Accordingly, an aspect of the invention involves a process for preparing 2,3,3,3-tetrafluoro-1-propene comprising: (a) contacting a starting material comprising 2-chloro-3,3,3-trifluoro-1-propene with hydrogen fluoride in the presence of a first activated catalyst selected from the group consisting of antimony-halides, iron-halides, titanium halides, and tin-halides, to produce an intermediate composition; and (b) contacting at least a portion of the intermediate composition with a second activated catalyst comprising carbon to produce a final product comprising 2,3,3,3-tetrafluoro-1-propene.

BRIEF DESCRIPTION OF THE DRAWINGS

FIG. 1 shows a schematic diagram of a preferred 2,3,3,3-tetrafluoro-1-propene synthesis process according to the invention.

DETAILED DESCRIPTION OF PREFERRED EMBODIMENTS OF THE INVENTION

Provided is a multi-step process for preparing 2,3,3,3-tetrafluoro-1-propene comprising two catalytic reactions. Preferably, the two catalytic reactions of the process are conducted separate reactors that are arranged in series. Referring to FIG. 1, the shown preferred process for 2,3,3,3-tetrafluoro-1-propene synthesis 1 involves one or more feed stream(s) 10 of HFO-1233xf and HF that are introduced into a first reactor 12, having a first catalyst bed 14, to produce an intermediate composition steam 20 comprising, for example, $CF_3CFClCH_3$ and/or $CF_3CF_2CH_3$. This intermediate composition stream 20 exits from the first reactor 12 and is then passed through column 26 which is packed with an HF scavenger 26, such as NaF, KF, or $Al_2O_3$, to remove a majority of, and preferably substantially all, the unreacted HF exiting the first reactor 12. The resulting cleaned intermediate composition stream 21 is then fed into a second reactor 22 having a second catalyst bed 24 to produce a final product stream 30 comprising HFO-1234yf. The final product steam 30 recovered from the second reactor 22 may optionally be passed through a scrubber 38 containing, for example, a KOH solution 36, to scrub HF and/or HCl from the steam, thereby yielding a cleaned final product stream 31.

Preferred catalysts for the first reaction include, but are not limited to, antimony halides, iron halides, titanium halides, and tin halides. More preferred catalysts are $SbCl_5$, $FeCl_3$, $TiCl_4$, and $SnCl_4$. Preferred antimony halides include antimony pentahalides, particularly those having the formula: $SbX_5$, wherein X is independently selected from Cl and F, with $SbCl_5$ being most preferred. Preferably, the first catalyst is supported by a substrate, such as carbon. Also, preferably the catalyst is arranged as bed that is disposed within the first reactor.

In highly preferred embodiments, the first catalyst is pretreated (i.e., activated) with $Cl_2$ and/or HF, and more preferably with both $Cl_2$ and HF, prior to use in the synthesis reaction. For example, an $SbCl_5$ catalyst supported on a carbon substrate can be activated by exposing the catalyst to 50 g/h of HF at 65° C. for 4 hours, then with the combination of about 50 g/h of HF and about 200 sccm of $Cl_2$ at about 65° C. for about 4 hours.

After pretreatment, free chloride is preferably removed from the catalyst surface. For example, after pretreatment about 50 sccm of $N_2$ can be passed over the catalyst bed for about 40 minutes to remove substantially all of the free chloride.

After the intermediate composition stream exits the first reactor, it preferably is processed to remove residual and/or unreacted HF from the stream. For example the intermediate composition stream can be passed through a column packed with NaF, KF, or $Al_2O_3$. The temperature of the packed column is preferably maintained at about 50-75° C. for high HF absorption efficiency.

Preferred catalysts for the second reaction are activated carbons. Acceptable activated carbons include those produced by Takeda Chemical Industries (marketed under the trade name SHIRO SAGI), Calgon Carbon Corp. (marketed under the trade name CARBOSORB™), Norit Americas Inc., and Aldrich (marketed under the trade name DARCO®). The second catalysts is preferably arranged as a bed that is disposed within the second reactor.

In one embodiment, the flow of material through the reactors is controlled by regulating the flow of the exit gases from the second reactor via a control valve, thus establishing a pressure drop though the system. That is, the flow of materials through the system is controlled by limiting the amount of material exiting the last second reactor and, thus, controlled pressure drops between subsequent components in the system is achieved. Preferably, the pressure in the first reactor is maintained at between about 40 and about 100 psig, more preferably from about 40 to 50 psig, whereas the pressure in the second reactor is maintained at between about 0 and about 100 psig, more preferably from about 5 to 10 psig, provided that the pressure in the second reactor is lower than the pressure in the first reactor.

Preferably, the temperature of the first reaction is maintained at about 140 to 200° C., more preferably from about 150 to 185° C. The temperature of the second reactor is preferably maintained at about 400 to 600° C., more preferably from about 450 to 550° C.

EXAMPLES

Certain aspects of the present invention are further illustrated, but are not limited by, the following examples.

Example 1

A 22-inch (½-inch diameter) Monel tube reactor, serving as the first reactor, was charged with about 120 cc of a 50-wt % $SbCl_5/C$ catalyst. The reactor was mounted inside a heater to maintain the reactor temperature. The temperature of the reaction was monitored by a thermocouple disposed at the middle inside of the reactor. The inlet of the reactor was connected to an electrical pre-heater, which maintained the inlet at 300° C. The pressure inside the reactor was maintained at about 45 psig.

A stream of HFO-1233xf at 70° C. and 150 sccm was fed from a cylinder through a regulator, needle valve, and a gas mass-flow-meter, and into the first reactor. This feed stream kept at a constant temperature of 73° C. by electrical heating to avoid condensation.

A stream of liquid HF was fed from a cylinder pressurized with $N_2$ at a constant pressure of 45 psig. The liquid HF flowed through a dip tube, needle valve, liquid mass flow meter, a research control valve, and a gate valve and then into the reactor at a rate of 50 g/h.

All feed cylinders were mounted on scales to monitor their weight by difference.

Samples of the gas mixtures exiting the first reactor were analyzed by on-line GC and GC/MS to determine their composition. It was found that the intermediate composition contained mainly $CF_3CF_2CH_3$ and $CF_3CFClCH_3$. The conversion of HFO-1233xf was about 50 to about 100% and the combined selectivity for $CF_3CF_2CH_3$ and $CF_3CFClCH_3$ was 90-97% depending on the temperature which was varied from about 148 to 175° C. (see Table A).

The product mixtures coming out of the first reactor were passed through a packed column containing NaF to separate HF from the stream. The packed column was kept at 50-75° C. for high HF adsorption efficiency.

The HF-free gas stream, thus obtained, was then passed into a second 22-inch (½-inch diameter) Monel tube reactor containing 120 cc of Calgon Activated Carbon. The interior temperature of the reactor was maintained at different temperatures from 400 to 550° C. (see Table A). The pressure of the second reactor was maintained at about 6 psig.

The exit gases from the second reactor were then passed through a 20-60-wt % aq. KOH scrubber solution to trap HF or HCl. The exit gases from the scrubber were condensed into a cylinder that was chilled with dry ice. The products were then isolated by distillation.

The results of the these tests are provided in Table A

TABLE A

| | (Reactor 1) | | (Reactor 2) | | Conversion HFO-1233xf (%) | Selectivity HFO-1234yf (%) |
|---|---|---|---|---|---|---|
| | Catalyst | Temp. (° C.) | Catalyst | Temp. (° C.) | | |
| 1 | 50 wt % $SbCl_5/C$ | 152 | Calgon | 400 | 83 | 55 |
| 2 | 50 wt % $SbCl_5/C$ | 155 | Calgon | 450 | 86 | 57 |
| 3 | 50 wt % $SbCl_5/C$ | 153 | Calgon | 500 | 89 | 59 |
| 4 | 50 wt % $SbCl_5/C$ | 148 | Calgon | 500 | 88 | 60 |
| 5 | 50 wt % $SbCl_5/C$ | 156 | Calgon | 550 | 90 | 77 |
| 6 | 50 wt % $SbCl_5/C$ | 175 | Calgon | 550 | 93 | 79 |

As seen in the data presented in Table A, the process described herein can be used to produce HFO-1234yf from HFO-1233xf at a conversion of over 90% and a selectivity of about 80%.

The separation of HF from the gas stream coming out off the first reactor is highly preferred for achieving high selectivity. Only 49% selectivity for HFO-1234yf was obtained when the exiting gas-stream of the first reactor was sent directly into the second reactor compare with 79% selectivity when HF separation was utilized.

Having thus described a few particular embodiments of the invention, it will be apparent to those skilled in the art, in view of the teachings contained herein, that various alterations, modifications, and improvements not specifically described are available and within the scope of the present invention. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A process for preparing 2,3,3,3-tetrafluoro-1-propene comprising:
    fluorinating a starting material comprising 2-chloro-3,3,3-trifluoro-1-propene by contacting said starting material with hydrogen fluoride in the presence of a first activated catalyst selected from the group consisting of antimony-halides, iron-halides, titanium halides, and tin-halides, to produce an intermediate composition; and dehydrohalogenating at least a portion of said intermediate composition by contacting said intermediate composition with a second activated catalyst comprising carbon to produce a final product comprising 2,3,3,3-tetrafluoro-1-propene.

2. The process of claim 1 wherein the fluorinating is performed in a first reactor and the dehydrohalogenating is preformed in a second reactor.

3. The process of claim 1 wherein said intermediate composition comprises at least one of $CF_3CFClCH_3$ and $CF_3CF_2CH_3$.

4. The process of claim 1 wherein said intermediate composition comprises both $CF_3CFClCH_3$ and $CF_3CF_2CH_3$.

5. The process of claim 1 wherein said first catalyst is supported on carbon.

6. The process of claim 5 wherein said first catalyst is selected from the group consisting of $SbCl_5$, $FeCl_3$, $TiCl_4$, and $SnCl_4$.

7. The process of claim 5 wherein said first catalyst is antimony pentahalide.

8. The process of claim 7 wherein said antimony pentahalide has the formula: $SbX_5$, wherein X is independently selected from Cl and F.

9. The process of claim 8 wherein said antimony pentahalide is $SbCl_5$.

10. The process of claim 1 wherein said first catalyst is activated by exposure to at least one of $Cl_2$ and HF.

11. The process of claim 10 wherein said first catalyst is activated by exposure to $Cl_2$ and HF.

12. The process of claim 1 wherein said fluorinating is performed at a temperature of about 100 to about 300° C. and a pressure of about 10 to about 200 psig.

13. The process of claim 1 further comprising:
removing at least a portion of unreacted HF from said intermediate composition prior to said dehydrohalogenation.

14. The process of claim 13 wherein said removing involves contacting said intermediate composition with at least one of NaF, KF, or $Al_2O_3$ at a temperature of about 20 to 100° C.

15. The process of claim 1 further comprising: contacting said final product with a scrubber solution or packed column to remove HF and/or HCl from said final product.

16. The process of claim 15 wherein said acid scavenger is a potassium hydroxide solution.

17. The process of claim 1 wherein said fluorinating and said dehydrohalogenating are conducted in the gas phase.

18. The process of claim 1 wherein said process has a conversion of said 2-chloro-3,3,3-trifluoro-1-propene of at least about 80% and a selectivity for 2,3,3,3-tetrafluoropropene of at least about 55%.

19. A process for preparing 2,3,3,3-tetrafluoro-1-propene comprising:
fluorinating a starting material comprising 2-chloro-3,3,3-trifluoro-1-propene by contacting said starting material with hydrogen fluoride in the presence of a first activated catalyst selected from the group consisting of antimony-halides, iron-halides, titanium halides, and tin-halides, to produce an intermediate composition;
removing at least a portion of unreacted HF from said intermediate composition; and
dehydrohalogenating at least a portion of said intermediate composition by contacting said intermediate composition with a second activated catalyst comprising carbon to produce a final product comprising 2,3,3,3-tetrafluoro-1-propene.

20. The process of claim 19 wherein said removing comprises contacting said intermediate composition with at least one of NaF, KF, or $Al_2O_3$ at a temperature of about 20 to 100° C.

21. The process of claim 1 wherein conditions of the fluorinating and dehydrohalogenating steps are effective to yield a conversion of 2-chloro-333-trifluoro-1-propene of greater than about 83%.

22. The process of claim 1 wherein conditions of the fluorinating and dehydrohalogenating steps are effective to yield a selectivity of 2,3,3,3-tetrafluoro-1-propene of greater than about 55%.

23. The process of claim 19 wherein conditions of the fluorinating and dehydrohalogenating steps are effective to yield a conversion of 2-chloro-333-trifluoro-1-propene of greater than about 83%.

24. The process of claim 19 wherein conditions of the fluorinating and dehydrohalogenating steps are effective to yield a selectivity of 2,3,3,3-tetrafluoro-1-propene of greater than about 55%.

* * * * *